United States Patent [19]

Putzier

[11] Patent Number: 5,262,218
[45] Date of Patent: Nov. 16, 1993

[54] ABSORBENT MATERIAL AND THE USE THEREOF

[75] Inventor: Heiner Putzier, Diessen, Fed. Rep. of Germany

[73] Assignee: Helen Harper Hygiene Vertriebs GmbH, Fed. Rep. of Germany

[21] Appl. No.: 908,216

[22] Filed: Jul. 2, 1992

[30] Foreign Application Priority Data

Jul. 5, 1991 [DE] Fed. Rep. of Germany ....... 4122359

[51] Int. Cl.$^5$ ............................................... B32B 1/04
[52] U.S. Cl. .................................... 428/74; 428/68; 428/76; 428/283; 428/284; 428/913; 604/367; 604/375
[58] Field of Search ............... 428/284, 283, 913, 68, 428/74, 76, 172; 604/367, 375

[56] References Cited

FOREIGN PATENT DOCUMENTS 0202127 11/1986 European Pat. Off. .
0418151 3/1991 European Pat. Off. .
3641893 6/1988 Fed. Rep. of Germany .

OTHER PUBLICATIONS

Wochenblatt Fur Papierfabrikation 1989 pp. 928-934 R. Lentz "Betrachtungen zur Umweltvertraglichkeit...".

*Primary Examiner*—James J. Bell
*Attorney, Agent, or Firm*—Hodgson, Russ, Andrews, Woods & Goodyear

[57] ABSTRACT

The invention concerns an absorbent material consisting of one or several layers permeable to liquids and an absorbing body having a high absorption and retention capacity for aqueous liquids, characterized by a structure consisting of a wrapper 1 made of a formed-fabric-type of material of an organic polymer, an intermediate tissue layer 2 made of an organic polymer, an absorbing body 3 composed of chemical pulp and an absorbent for aqueous liquids and a binder stabilizing the wrapper as well as the use of said absorbent materials for the production of absorbent bodies, inlays and pads.

The invention also concerns a structure comprising such an absorbent material in combination with a wrapper impermeable to liquids.

17 Claims, 1 Drawing Sheet

ABSORBENT MATERIAL AND THE USE THEREOF

The present invention concerns an absorbent material composed of one or several layer(s). In particular, the invention concerns a multi-layer, absorbent material the components of which are decomposable under biological conditions, for example compostable or humifiable. In addition, said invention concerns the use of a material of this type as inlays for diapers, hygiene inlays and pads, respectively, protective pads against incontinence an such like as well as structures comprising an absorbent material of this type.

In the field of hygiene and incontinence articles, absorbent materials have been developed of late that not only differ from previous known materials in that they can absorb large quantities of liquid within a very short period of time, but also in that said materials have a chemical structure enabling them to retain this liquid without causing a feeling of humidity in the places of the body concerned. Both the absorbency and the capacity of retention of absorbent materials for the above-mentioned purposes have been gradually improved upon. Especially in the fields of diapers and diaper inlays, respectively, materials permitting longer intervals between changing the infants have been developed. In this respect, so-called "one-piece systems" comprising an absorbent inner body and an outer wrapper primarily composed of a synthetic, water-resistant polymer were increasingly provided. These systems permit a complete disposal of the entire "piece" including the faeces or body liquids contained therein. This was widely regarded as an additional convenience in infant care.

The consideration that these so-called "one piece systems" contribute to a further increase in the already critical refuse volume was apparently not taken into account in this respect. In particular, these systems contribute to the refuse being charged with materials than cannot be decomposed by natural chemical processes; instead, these practically non-rotting materials must be stored in refuse dumps or be decomposed by both cost and time consuming pyrolytic processes (refuse combustion).

In the quest to avoid a further increase in the refuse volume or perhaps to even reduce it, experts in this field have recently returned to the so-called "two-piece systems" which had been customary in the past, but had been regarded as too inconvenient. As a rule, such "two-piece systems" comprise an absorbent inner body that is changed regularly as well as a washable outer wrapper suitable for repeated use. Such a system could help reduce the refuse volume resulting from hygiene pads, diapers, incontinence materials and such like to a certain extent.

So far, nothing was known about a possible biological decomposability of the "two-piece systems" suggested in this context. In the course of the above-mentioned quest, however, there has been a significant demand of late for absorbent inlays for diapers, hygiene articles such as ladies' sanitary pads or incontinence pads and such like which are decomposable under biological conditions, i.e. compostable or humifiable.

Therefore, it was the object of the present invention to provide an absorbent material having a high absorption and retention capacity.

It was a further object of the invention to provide an absorbent material having a high absorption and retention capacity for body liquids. In the context of the present application and the patent claims, "body liquids" are defined as sweat, phlegm, blood, urine, faecal secretions and such like.

It was a further object of the invention to provide absorbent materials with a high absorption and retention capacity which are decomposable under biological conditions, i.e. which can, for example, be composted or even humified without the addition of chemicals and/or under environmental conditions and which therefore do not contribute significantly to the refuse volume.

It was a further object of the invention to indicate suitable uses for such an absorbent material and to provide structures comprising said absorbent material.

Surprisingly, it was found that it is possible to provide absorbent materials having a high absorption and retention capacity for body liquids by combining wrappers made of materials of a natural origin, particularly of plant origin, with absorbent materials also obtained from natural sources, especially plant materials, and integrating into said combination chemical substances which have a high absorbency of liquids and which, owing to their chemical structure, are suitable for decomposition under biological conditions. Surprisingly, it was also found that such materials are, if at all, only slightly inferior to the synthetic materials known so far with regard to absorbency and liquid retention. However, any possible disadvantage of a reduced absorbency is more than compensated by the improved biological decomposability or compostability, respectively.

The invention concerns an absorbent material consisting of one or several layers permeable to liquids and an absorbing body having a high absorption and retention capacity for aqueous liquids, characterised by an absorbency of at least 8 g/g, a retention capacity of at least 6 g/g and a structure comprised of (a) a wrapper (1) of a formed-fabric-type material made of an organic polymer;
(b) an intermediate tissue layer made of an organic polymer;
(c) an absorbing body composed of chemical pulp having a specific volume of at least 15 cm$^3$/g and an absorbency of at least 8 g and an absorbent for aqueous liquids having a particle size of 80 to 1,000/$\mu$m and a bulk volume of at least 300 kg/m$^3$; and
(d) a binder stabilising the wrapper.

The invention also concerns the use of such an absorbent material for the production of absorbent bodies, inlays and pads in the areas of infant care, incontinence and personal hygiene.

The invention also concerns structures comprising an absorbent material of the above-mentioned type in combination with a wrapper impermeable to liquids.

Preferred embodiments of the invention result from the sub-claims.

The invention will now be described in greater detail with the aid of the enclosed figures.

Figure 1:
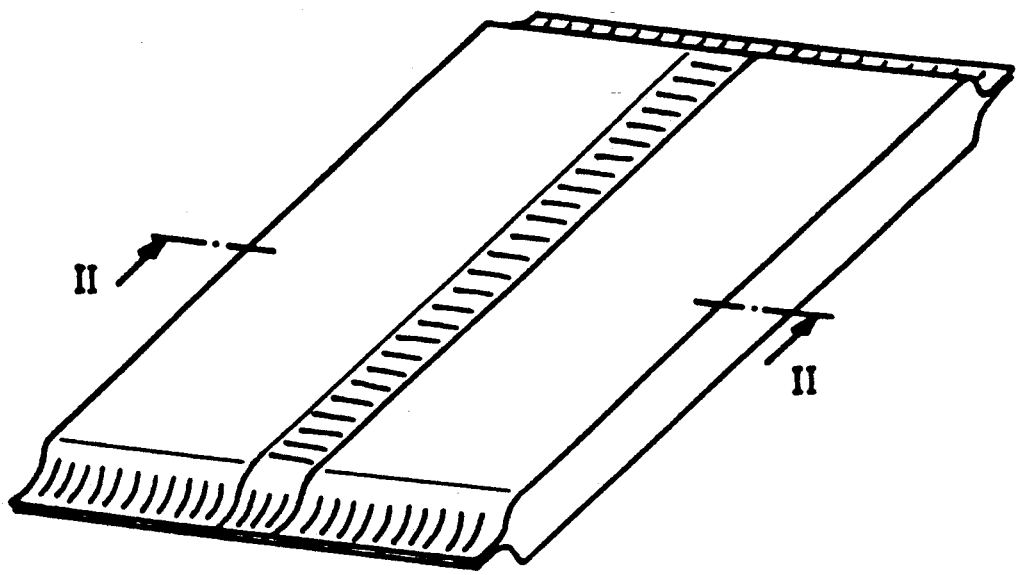
FIG. 1 shows a total view of a preferred embodiment of the absorbent material according to the invention ready for use without limiting the invention to this embodiment.
Figure 2:
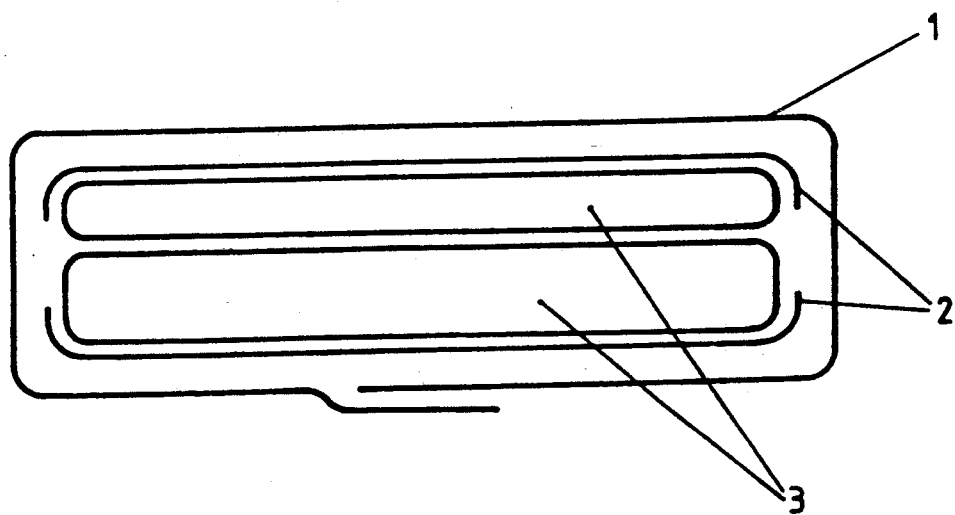
FIG. 2 shows a cross-section through a preferred embodiment of the absorbent material according to the invention without the invention necessarily having to comprise all the individual components shown in this figure.

The absorbent material according to the invention is composed of one or several layers permeable to liquids or absorbing liquids, respectively. Liquids are primarily understood to be such body liquids as listed in detail above as an example. It is the meaning and the purpose of the permeable layers to permit an optimal passage or distribution, respectively, of the above-mentioned liquids into the inner part of the absorbent material according to the invention and thus to prevent the surface of the absorbent material from contacting the skin in the humid state. Owing to the ingredients of the above-mentioned liquids, this would result in the skin parts concerned becoming sore and should therefore be avoided. The liquids in question are absorbed in the inner part of the absorbent material.

An absorbing body arranged on the inside of the material and separated from its environment by at least one of the above-described layers permeable to liquids is another component of the absorbent material according to the invention. Said absorbing body has a high absorption and retention capacity for aqueous liquids, especially the body liquids given as an example above. According to the invention, the material of the absorbing body has an absorption capacity for aqueous liquids of at least 8 g/g, preferably in the range of 8 to 14 g/g, especially preferably in the range of 10 to 12 g/g.

Another characteristic feature of the absorbing body is its retention capacity for the above-mentioned aqueous liquids. According to the invention, said retention capacity is at least 6 g/g, preferably in the range of 12 to 40 g/g, especially preferably 18 to 30 g/g. The advantage according to the invention of the above-mentioned absorption and retention capacity values lies in the fact that aqueous liquids are absorbed within a short period of time and, owing to the chemical structure of the materials involved, are retained rather than being released to the environment. This can, for example, be effected by a part of the components of the absorbing body swelling up owing to its chemical structure when liquid is added and thus preventing release of said liquid to the environment. However, the actual mechanism of absorption and retention is not limited to this chemical phenomenon.

According to the invention, the absorbing body (3) of the absorbent material is composed of chemical pulp ("fluff") and an absorbent for aqueous liquids. Absorbents for aqueous liquids are understood to be substances that absorb this type of liquids and are capable of retaining a comparatively high percentage of said liquids, possibly even under pressure. According to the invention, the absorbing body (3) accounts for approx. 80 to 90 wt. % of the absorbent material, preferably 85 to 87 wt. %. The weight ratio of the two components "fluff" and absorbent inside the absorbing body is in the range of 9:1 to 14:1, a ratio of approx. 12:1 being preferred.

The chemical pulp has the following characteristics: According to the object of the present invention, namely to provide absorbent materials decomposable under biological conditions, for example compostable or humifiable materials, only chemical pulp without components harmful to the environment is used. According to the invention, a material produced under conditions that have the least damaging effect on the environment is especially preferred. In a specially preferred embodiment, for example, chemical pulp is used that was either bleached without chlorine or was not subjected to any bleaching process.

The material of the chemical pulp should have high wettability. The specific volume of the chemical pulp used according to the invention is at least 15 $cm^3/g$, preferably at least 20 $cm^3/g$. The absorbency of the chemical pulp of the absorbing body is at least 8 g/g, preferably 8 to 12 g/g. The person skilled in the art knows additional materials for the same purpose which can also be used without making any difference, provided the object of the present invention, namely to compost the absorbent materials under biological conditions, is not jeopardised.

The absorbent for aqueous liquids used for the absorbent material according to the invention has a particle size in the range of 80 to 1,000 mm, preferably 200 to 600 mm, especially preferably approx. 400 mm. In addition, it has a bulk volume of at least 300 $kg/m^3$, preferably 350 to 450 $kg/m^3$, in preferred embodiments.

In a preferred embodiment of the invention, the absorbent is selected from the group of high-molecular water-soluble polyelectrolytes on polyacrylate basis, carboxy methyl cellulose and grafted starch. Materials of this type are known as such in the prior art and are available commercially. By way of an example in this context, the author would like to mention the so-called superabsorbents which are very strong polyelectrolytes and, owing to their high molecular weight, are not soluble in water. The superabsorbents suitable according to the invention have an extremely high attractivity to water. They can either be derived from completely natural products or be chemically modified products of natural origin. Examples preferred according to the invention are carboxy methyl cellulose, polyacrylates and grafted starch, especially starch grafted with acryl groups. The acrylate groups can be neutralised with suitable metal ions, preferably alkali metal ions and/or alkaline-earth metal ions that are physiologically acceptable and not damaging to biological decomposability. Suitable products, for example, are known under the trade name Akucell®SW by Akzo or under the product name Drystar®H 20 and H 40 by Starchem or under the product name Sanwet® M 500 S by Hoechst AG.

In specially preferred embodiments, for example, these products have a pH value (0.5% in 1% NaCl solution) in the neutral to slightly acid pH value range, e.g. pH 6, and have an absorbency (centrifugation) in the range of 25 to 50 g/g, preferably 30 to 45 g/g; it is possible to use an aqueous liquid such as urine, for test purposes, especially synthetic urine, as the absorbed liquid. In this preferred case, the retention capacity for the same aqueous liquid is in the range of 10 to 40 g/g, preferably in the range of 15 to 30 g/g. Such materials are available commercially in the shape of free-flowing white powder granules which remain granule-type gel particles even after liquid has been absorbed, i.e. after they have swollen up.

In addition to the absorbing body (3), a wrapper (1) made of a formed-fabric-type material of an organic polymer ("coverstock") is also part of the structure of the absorbent material according to the invention. In a preferred embodiment of the invention, the wrapper or coverstock is made of a non-woven material of an organic polymer of plant origin. Especially preferred are non-woven substances of cotton-type materials which, for example, account for 5 to 8 wt. %, preferably 6 to 7 wt. %, of the entire material. Such materials are available commercially in various embodiments. Other materials, for example rayon stable fibres/viscose, are also possible beside cotton. Also suitable are viscose fibres available under the name Rayon ®, provided they are decomposable under biological conditions. Such materials (non-wovens) are supplied, for example, by the Lohmann company under the name Paraprint OL 25 P 20. Needless to say, materials made of other organic polymers, especially organic polymers of plant origin, are also suitable.

In another preferred embodiment of the invention, the wrapper or coverstock (1) is arranged in such a way that the absorbent material is completely enclosed. By means of a suitable binder this structure is stabilised in such a way that the material of the absorbing body, i.e. the "fluff" (cellulose) and/or the absorbent for aqueous liquids, cannot escape. This embodiment is considered to be especially advantageous, because the above-mentioned arrangement prevents components of the absorbent material according to the invention from escaping from the overall structure before, during or after use, thereby reducing the practical value of the material.

In a further preferred embodiment of the invention the superabsorber in the "fluff" is stabilised not only by the use of a suitable binder, but by providing the absorbent material with a suitable embossing, for example a rhomb-shaped embossing known per se from the prior art. This causes the absorbent material to be compressed in such a way that the volume of the fluff is significantly reduced and the particles of the superabsorber in the absorbing body are more or less immobilised. Consequently, the superabsorber can no longer escape. Another advantageous effect obtained by embossing is that it creates "channels" which permit a comparatively rapid passage of the entering liquid from the point of entry to the surrounding area, making possible an equal distribution over a larger area of the absorbing body. The embossing process is carried out by a method known per se in the art, for example by feeding the absorbent material (chemical pulp (cellulose) together with the superabsorber and the binder) through suitable rollers.

In another preferred embodiment of the invention, the binder comprises compounds from the group of EVA polymers or related polymers, possibly with additional polymerisable olefin monomers. Suitable for this purpose, but not limiting the invention, is a binder called H 331 plus supplied by Ecomelt or a binder called Dispomelt 127 made by National Starch & Chemical B.V.

Another component of the absorbent material according to the invention is an intermediate tissue layer (2) made of an organic polymer and having the purpose of fixing the absorbing body and distributing the liquid to be absorbed. In a preferred embodiment, said intermediate layer also consists of cellulose or modified cellulose, respectively, i.e. "fluff" materials in the widest sense, and accounts for 3 to 6 wt. %, preferably approx. 4 to 5 wt. %, of the entire material.

With the aid of the above-described structure, there is provided an absorbent material having an absorption and retention capacity for aqueous liquids which is at least equally effective as that of materials from the prior art. However, it was the all-important object of the present invention to provide absorbent materials which are decomposable under biological- conditions. This object is achieved by the absorbent material according to the invention. Owing to its structure which is exclusively composed of organic polymers of natural origin or of polymers derived from such natural polymers by a simple chemical reaction, an absorbent material which is completely harmless to the environment and decomposable by natural chemical reactions is obtained. Owing to its similarity or identical structure with natural materials, said absorbent material can be decomposed, at least to a large extent, by micro-organisms active in composting and humifying processes under natural conditions and without the addition of any chemicals. This makes it possible to organise the disposal of the materials in question in such a way that the non-rottable refuse volume does not increase further.

In cases where a complete biological decomposition under the influence of the micro-organisms that are active during composting or humification, respectively, is not possible and where the compost or humus materials are to be worked into the soil later on, residues of superabsorber or binder which have not decomposed completely can contribute to loosening the soil on the one hand and to improve the liquid retention capacity on the other hand. These materials remain in the ground for a comparatively long time and play a role not only in keeping the topsoil loose under the influence of humidity but also in retaining water in the relevant soil layer for a certain period of time rather than allowing it to seep through directly. In this case it must be kept in mind that the portion of the humified material originating from the absorbent materials according to the invention is comparatively small and therefore remains in the range which is just sufficient to improve the physical properties of the soil.

According to the invention, the above-described absorbent material is used for the production of absorbent moulded bodies, inlays and pads in the fields of infant care, incontinence and personal hygiene. By way of example, inlays for diapers, incontinence inlays or pads and ladies' sanitary pads should be mentioned. Especially in the range of use "inlays for diapers" the desired "two-piece system" solution can be successfully realised. The advantage of using the materials according to the invention is not only due to the satisfactory absorption and retention capacity of said materials for aqueous liquids, but also to the biological decomposability and therefore environmentally harmless disposal thereof.

The invention also concerns a structure comprising an absorbent material as described in detail above in combination with a wrapper impermeable to liquids. Said wrapper ensures the secure fit of the material according to the invention, thus preventing any liquid from escaping. Without limiting the invention, said wrapper can, for example, be a diaper panty which, in line with the object of the invention to save raw material, can be made of a material impermeable to liquid and suitable for multiple use (possibly after washing). Proven wrappers are, for example, those cut in panty shape and available under the trade name Darlexx ®. The material, for example, is described in U.S. Pat. No. 4,761,321. Other wrappers impermeable to liquids are, for example, pads for incontinence articles on a suitable basis, for example on the basis of the material Darlexx ®.

Of late, physiological facts were especially taken into account in the production of diapers by developing differing types of diapers for boys and girls. The invariable disadvantage of this solution was the necessity to provide a different type of diaper for each sex.

The "two-piece system" solution according to the invention facilitates supplying boys and girls with different absorbent materials in an astounding manner. This is simply done by distributing for example 80% of the total quantity of superabsorbent in a volume of absorbent material corresponding to approx. two-thirds of the surface. This area of absorbent material naturally has a better absorbency than the area where the total quantity of superabsorbent is noticeably lower. By marking the absorbent material in a manner visible from outside, said absorbent material can be shifted in the diaper panty or in the hygiene pad or in the incontinence pad, respectively, in such a way that the sex-specific occurrence of liquid is accounted for.

The invention is illustrated in detail by the following example:

EXAMPLE

With the aid of 20 mothers of infants a test was carried out wherein the babies were changed into structures according to the invention, i.e. the absorbent materials and a wrapper impermeable to liquid in the shape of a diaper panty according to the invention.

During the three-month test period the infants did not suffer from skin irritations or other complaints. The functionality of the "two-piece system" was also proven with a view to the fact that one absorbent material could be used for both boys and girls.

In comparison with traditional diapers, the mothers also found that unpleasant odours were reduced. Apparently the diaper panty is more permeable to air than the plastic foil used in industry-made diapers. This minimises the development of unpleasant odours.

After use, the absorbent materials were kept separately and collected once a week. They were then shredded under supervision in a compost plant and composted together with other compostable garden and kitchen refuse. With the purpose of improving the soil, they were then spread over arable areas by local farmers.

The farmers were satisfied with the resulting improvements to the soil. Especially favourable were the comments on the increased humidity retention capacity of the soil caused by the superabsorbent which had not been decomposed microbiologically.

I claim:

1. An absorbent material comprising one or several liquid-permeable layer and an absorbing body having a high absorption and retention capacity for aqueous liquids, characterised by an absorbency of at least 8 g/g and a retention capacity of at least 6 g/g as well as a structure comprising
   a) a wrapper (1) of a formed-fabric-type material made of an organic polymer;
   b) an intermediate tissue layer (2) contained in said wrapper and made of an organic polymer;
   c) an absorbing body (3) contained in said wrapper and composed of chemical pulp having a specific volume of at least 15 $Cm^3/g$ and an absorbency of at least 8 g and a particulate absorbent for aqueous liquids having a particle size of 80 to 1,000 $\mu m$ and a bulk volume of at least 300 $kg/m^3$; and
   d) a binder stabilizing the wrapper (1).

2. An absorbent material according to claim 1, wherein the wrapper (1) consists of a formed fabric made of an organic polymer of plant origin.

3. An absorbent material according to claim 2, wherein the wrapper (1) is a formed fabric made of cotton or of rayon staple fibre/viscose.

4. An absorbent material according to one of several or the claims 1 to 3, wherein the wrapper (1) is the outer layer extending all the way round the material, said wrapper (1) being stabilised by a binder in such a way that the material of the absorbing body cannot escape.

5. An absorbent material according to one or several of the claims 1 to 3, wherein the binder is selected from the group of EVA polymers and related polymers, which may be in combination with additional polymerisable olefin monomers.

6. An absorbent material according to one or several of the claims 1 to 3, wherein the intermediate tissue layer (2) consists of chemical pulp.

7. An absorbent material according to one or several of the claims 1 to 3, wherein the absorbing body (3) consists of chemical pulp and an absorbent at a weight ratio of 9:1 to 14:1, a ratio of approx. 12:1 being desirable.

8. An absorbent material according to one or several of the claims 1 to 3, wherein the absorbent is selected from the group of high-molecular water-soluble polyelectrolytes on a polyacrylate basis, carboxy methyl cellulose and grafted starch, especially acrylate-grafted starch neutralised with physiologically acceptable alkali metal ions or alkaline-earth metal ions.

9. An absorbent material according to one or several of the claims 1 to 3, wherein the absorbent has an absorbency in the range of 25 to 50 g/g.

10. An absorbent material according to one or several of the claims 1 to 3, wherein the absorbent has a retention capacity in the range of 10 to 40 g/g.

11. An absorbent material according to one or several of the claims 1 to 3, wherein the chemical pulp of the absorbing body (3) has an absorbency in the range of 8 to 12 g/g.

12. The absorbent material according to one or several of the claims 1 to 3 for the production of absorbent bodies, inlays and pads in the areas of infant care, incontinence and personal hygiene.

13. Absorbent material according to claim 12 for diaper inlays.

14. Absorbent material according to claim 12 for incontinence pads.

15. Absorbent material according to claim 12 for sanitary pads.

16. A structure comprising an absorbent material according to one or several of the claims 1 to 3 in combination with a wrapper impermeable to liquids.

17. A structure according to claim 16, wherein the wrapper impermeable to liquids is a diaper panty.

* * * * *